(12) United States Patent
Farrar et al.

(10) Patent No.: US 8,992,614 B2
(45) Date of Patent: *Mar. 31, 2015

(54) TISSUE REPAIR AND REPLACEMENT

(71) Applicant: Smith & Nephew, Inc., Memphis, TN (US)

(72) Inventors: David Farrar, York (GB); Malcolm Brown, Otley (GB); Michael Hall, Linthorpe (GB); John Eric Brunelle, Boston, MA (US); Nicholas John Cotton, Westborough, MA (US); Rod Berube, North Attleboro, MA (US); John Lipchitz, Watertown, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/961,507

(22) Filed: Aug. 7, 2013

(65) Prior Publication Data

US 2013/0323294 A1   Dec. 5, 2013

Related U.S. Application Data

(63) Continuation of application No. 10/645,962, filed on Aug. 22, 2003, now Pat. No. 8,529,625.

(51) Int. Cl.
*A61F 2/28* (2006.01)
*A61L 27/48* (2006.01)
*A61L 24/00* (2006.01)
(Continued)

(52) U.S. Cl.
CPC ............ *A61L 27/48* (2013.01); *A61L 24/0036* (2013.01); *A61L 24/0042* (2013.01); *A61L 24/0063* (2013.01); *A61L 24/0084* (2013.01); *A61L 24/0094* (2013.01); *A61L 27/425* (2013.01); *A61L 27/46* (2013.01); *A61L 27/56* (2013.01); *A61L 27/58* (2013.01); *A61L 27/14* (2013.01)
USPC ....................................... 623/16.11

(58) Field of Classification Search
USPC ............................. 623/16.11, 23.75
See application file for complete search history.

(56) References Cited

U.S. PATENT DOCUMENTS 4,373,217 A   2/1983   Draenert
4,849,285 A   7/1989   Dillon
(Continued)

FOREIGN PATENT DOCUMENTS

WO   9745147   12/1997
WO   9846164   10/1998
(Continued)

OTHER PUBLICATIONS

Nam, Y. et al., Journal of Biomedical Materials Research, "Porous biodegradable polymeric scaffolds prepared by thermally induced phase separation", pp. 8-17, (1998).
(Continued)

*Primary Examiner* — Suzette J Gherbi
(74) *Attorney, Agent, or Firm* — David L. Fox; JL Salazar Law Firm

(57) ABSTRACT

Tissue fixation devices are provided. The devices include a first component and a second component, the components having different rates of in vivo degradation. The first component and second component are arranged so that, upon degradation of one of the components, the other component provides a scaffold into which bone can grow.

18 Claims, 3 Drawing Sheets

(51) Int. Cl.
*A61L 27/42* (2006.01)
*A61L 27/46* (2006.01)
*A61L 27/56* (2006.01)
*A61L 27/58* (2006.01)
*A61L 27/14* (2006.01)

(56) References Cited

U.S. PATENT DOCUMENTS

| | | | |
|---|---|---|---|
| 5,589,176 A * | 12/1996 | Seare, Jr. | 424/400 |
| 5,605,693 A | 2/1997 | Seare, Jr. | |
| 6,110,484 A | 8/2000 | Sierra | |
| 6,306,169 B1 | 10/2001 | Lee et al. | |
| 6,337,198 B1 | 1/2002 | Levene et al. | |
| 6,344,496 B1 | 2/2002 | Niederauer et al. | |
| 6,376,573 B1 | 4/2002 | White et al. | |
| 6,583,232 B1 | 6/2003 | Brown | |
| 6,599,323 B2 | 7/2003 | Melican et al. | |
| 6,605,293 B1 | 8/2003 | Giordano et al. | |
| 7,066,962 B2 | 6/2006 | Swords | |
| 7,122,057 B2 | 10/2006 | Beam et al. | |
| 2003/0003127 A1 * | 1/2003 | Brown et al. | 424/423 |
| 2003/0072790 A1 | 4/2003 | Lai et al. | |
| 2003/0114936 A1 | 6/2003 | Gaylo et al. | |
| 2003/0186005 A1 | 10/2003 | D'Alessio et al. | |
| 2003/0219466 A1 | 11/2003 | Campbell | |
| 2003/0236573 A1 | 12/2003 | Evans et al. | |
| 2004/0002770 A1 | 1/2004 | King et al. | |
| 2005/0031704 A1 | 2/2005 | Ahn | |
| 2005/0163822 A1 | 7/2005 | Shirahama et al. | |
| 2005/0209705 A1 | 9/2005 | Niederauer et al. | |
| 2006/0004030 A1 | 1/2006 | Ebden et al. | |
| 2008/0015709 A1 | 1/2008 | Evans et al. | |

FOREIGN PATENT DOCUMENTS

| | | |
|---|---|---|
| WO | 9847445 | 10/1998 |
| WO | 0132072 | 5/2001 |
| WO | 0191789 | 12/2001 |
| WO | 0215881 | 2/2002 |
| WO | 2004014439 | 2/2004 |
| WO | 2004018435 | 3/2004 |
| WO | 2004075862 | 9/2004 |

OTHER PUBLICATIONS

Washburn, N.R., et al., Journal of Biomedical Materials Research, "Co-extrusion of biocompatible polymers for scaffolds with co-continuous morphology", pp. 20-29, (2001).
International Search Report and Written Opinion for PCT Patent Application No. PCT/US2004/027309 dated Feb. 7, 205, 11 pages.
International Preliminary Report on Patentability for PCT Patent Application No. PCT/US2004/027309 dated Oct. 8, 2005, 8 pages.
"Review of in vivo fate of GRC DL-Lactide with a TCP scaffold in cancellous bone of sheep", date unknown but prior to the date of this application.
Anderson, M., "Smith and Nephew Research Centre Work Report", pp. 1-7, date unknown but prior to the date of this application.
Roe, J., et al., "Randomised controlled trial of osteoconductive fixation screws for ACL reconstruction. A comparison of the Calaxo and the Milagro screw. 12 month results", American Academy of Ortheopedic Surgeons Annual Meeting, New Orleans, 2010.
English translation and Japanese Office Action for Patent Application No. 2006-524105 dated Jan. 25, 2011, 10 pages.
Response to Office Action for European Patent Application No. 04781909.9 dated Jul. 13, 2009, 19 pages.
Office Action for European Patent Application No. 04781909.9 dated Jan. 14, 2009, 2 pages.
Search Report and Written Opinion for PCT Application No. PCT/US2004/027309 dated Feb. 14, 2005, 10 pages.

* cited by examiner

TISSUE REPAIR AND REPLACEMENT

TECHNICAL FIELD

This invention relates to tissue repair and replacement, and more particularly to methods and devices for repairing and/or replacing hard and soft tissue, e.g., orthopedic fixation devices, bone graft substitute materials, and wound dressings.

BACKGROUND

The development of materials for tissue fixation devices has proceeded rapidly in recent years. The use of biodegradable polymers in such devices has provided surgeons with a safe alternative to metallic implants, potentially reducing adverse tissue response and eliminating the presence of a permanent tissue defect or the need to surgically remove the implant.

Ideally, biodegradable tissue fixation devices should provide long-term repair strength, complete healing of the defect site, and controlled resorption of the device by the body. Biodegradable tissue fixation devices should have sufficient mechanical strength to withstand loads encountered during the healing process, while also providing an open "scaffold" structure that allows full bone ingrowth and remodeling.

Thermally-induced phase separation of polymer solutions and blends has been used to form porous biodegradable scaffolds for tissue engineering (see, e.g., J Biomed Mater Res, 47:8-17, 1999 and J Biomed Mater Res 60:20-29, 2002.) For example, polymeric scaffolds may be formed by heat treating a blend of soluble and insoluble polymers to increase phase separation, and then dissolving the soluble polymer to leave a porous scaffold of the insoluble polymer. These scaffolds are formed prior to implantation, i.e., the scaffold is porous when it is implanted into a patient.

Porous ceramic materials, e.g., porous calcium phosphate ceramics, have been used as bone graft substitutes. While these materials may promote bone cell attachment and infiltration, they are typically brittle, and thus may not possess the mechanical strength needed for use in tissue fixation devices.

SUMMARY

In general, the invention features biodegradable tissue fixation devices that are substantially non-porous prior to implantation, providing a mechanically robust anchor during implantation and initial use. By "substantially non-porous," we mean that the mechanical strength of the device is not compromised by any porosity, as compared to the mechanical strength of a similar device of the same material having no porosity, i.e., being fully dense. Generally, the compressive strength of the device, as measured by ASTM D695, is at least 80% of that of a similar device formed of fully dense material. Typically, the devices, when initially implanted, do not have sufficient porosity to support tissue ingrowth.

The tissue fixation devices include at least two components having different relative rates of in vivo degradation. The components form co-continuous interpenetrating phases so that, after the device is implanted in a patient, the faster-degrading component degrades in vivo leaving a macro-porous scaffold formed of the other component. The scaffold has pores into which tissue, e.g., bone, can infiltrate, allowing good tissue ingrowth and remodeling. The component that forms the scaffold may be relatively non-degradable, or may eventually degrade.

In one aspect, the invention features a tissue fixation device that includes a blend of two polymers with different rates of in vivo degradation. The two polymers are immiscible and have a co-continuous macroscopic phase-separated structure. The size scale for the phase-separated structure may be up to 3500 microns, e.g., 50-1000 microns, typically 200-1000 microns.

In another aspect, the invention features a tissue fixation device that includes a porous ceramic structure and a polymer disposed in pores of the ceramic structure. The polymer may have a higher rate of in vivo degradation than the ceramic, resulting in a ceramic scaffold after in vivo degradation. Alternatively, the ceramic may have a higher rate of in vivo degradation, resulting in a polymeric scaffold after in vivo degradation. In some implementations, the component forming the scaffold is substantially non-degradable in vivo.

In a further aspect, the invention features a tissue fixation device that includes a porous polymeric structure and a ceramic material disposed in pores of the polymeric structure, the ceramic having a higher rate of in vivo degradation than the polymer.

In yet another aspect, the invention features a tissue fixation device that includes two interpenetrating ceramic materials, one ceramic material having a higher rate of in vivo degradation than the other.

The devices discussed above may have one or more of the following advantages.

The devices are initially non-porous and so have good strength and stiffness, enabling them to function well in use. In some implementations, the device may have a compressive strength (ASTM D695) of at least 10 MPa. When the devices degrade in vivo, the pores within the resulting scaffold are above the size required for tissue ingrowth, facilitating ingrowth of bone or other tissue into the device. This tissue ingrowth, especially in the case of bone, will enhance the strength of the repair.

The slow-degrading component that forms the scaffold maintains the mechanical properties and functionality of the device, as the rapid-degrading component is replaced by ingrowing tissue. The scaffold material (slow-degrading polymer or ceramic) may subsequently degrade, leaving pores in the tissue that replaced the rapid-degrading component.

The porous structure of the scaffold allows a controlled release of breakdown products, which may prevent undesirable "burst release" of breakdown products.

The details of one or more embodiments of the invention are set forth in the accompanying drawings and the description below. Other features and advantages of the invention will be apparent from the description and drawings, and from the claims.

DETAILED DESCRIPTION

Figure 1:
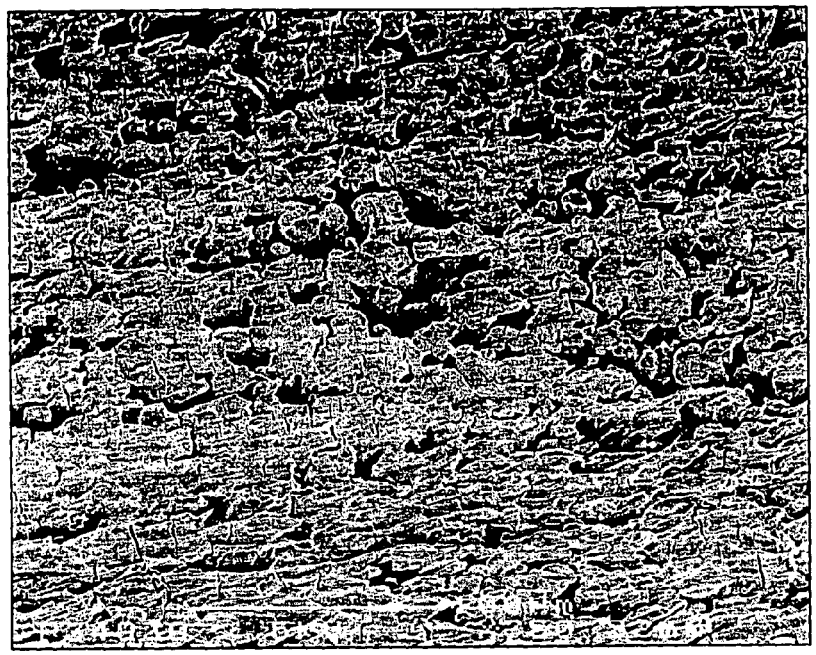
FIGS. 1 and 2 are SEM photomicrographs of a polymeric scaffold resulting from the procedures described in Example 1.

Biodegradable tissue fixation devices are provided that are initially substantially non-porous. The devices include two or more components, present as co-continuous interpenetrating phases, having different rates of in vivo degradation. After implantation, the faster-degrading component degrades first, leaving a porous scaffold of the slower-degrading component. The slower degrading component may then degrade, leaving pores in the ingrowing tissue, or, in some cases, may remain intact for the life of the implanted device.

As will be discussed in detail below, the device may include, for example, (i) two polymeric components; (ii) a polymeric component and a ceramic component, with the polymeric component being faster degrading and the ceramic component forming the scaffold; (iii) a polymeric component and a ceramic component, with the ceramic component being faster degrading and the polymeric component forming the scaffold; or (iv) two ceramic components. In the case of two polymeric components, the device may be formed by phase separation of a blend of immiscible polymers, or by initially forming a polymeric scaffold of a first polymer, and infiltrating the pre-formed scaffold with a second polymer. These various options will be discussed in turn below.

Devices Including Two Polymeric Components (Polymer-Polymer Systems)

From Polymer Blends

As discussed above, initially non-porous biodegradable tissue fixation devices may be formed using a blend of two bioresorbable polymers with different rates of in vivo degradation. The two polymers are immiscible and have a co-continuous macroscopic phase-separated structure. Generally, the two polymers are insoluble in water or aqueous media, e.g., body fluids.

Immiscible polymer blends, when melted, generally behave as an emulsion. However, due to the relatively high viscosity of the melted polymers, phase separation and inversion occurs only very slowly. This allows control of the size of the phases and production of co-continuous phase structures at compositions other than phase inversion point. If a well-mixed immiscible polymer blend is heated above its melting point its phases will slowly separate to produce a co-continuous or discontinuous phase structure.

Generally, the phases should be substantially co-continuous, so that the pores produced during degradation will be interconnected. If the rapid-degrading phase is discontinuous, degradation products may not be able to escape from the scaffold and tissue may not be able to grow in. If the slow-degrading phase is discontinuous the scaffold produced when the polymer degrades may not have adequate structural integrity.

The structure of the phases can be controlled by the choice of polymers, e.g., based on their miscibility, melt viscosities and molecular weights, and by the ratio of the polymers. The polymers and the ratio in which they are provided are selected so that a co-continuous phase separated structure is provided.

The criteria for choosing a pair of polymers are that the two polymers (a) degrade at different rates, so that a porous scaffold is formed before the entire device degrades; and (b) be immiscible, so that they form two separate phases when mixed.

Degradation rate can be quantified as the time required for 100% mass loss. A particular component can serve as the fast-degrading component in one polymer blend, and yet serve as the slow-degrading component in a different polymer blend. For example, polyglyconates are fast-degrading compared to PLLA, but slow degrading compared to polyanhydrides. The table below shows some degradation rates (100% mass loss) for some common bioresorbable polymers. Degradation rates were tested according to ISO 15814 "Implants for Surgery—Copolymers and blends based on polylactide—In-vitro degradation". Briefly, this test method involves placing samples in phosphate buffer solution at pH 7.4 at 37° C. Samples are removed at desired time intervals and weighed to determine mass loss, mechanical properties, molecular weight etc. The test conditions are intended to simulate in vivo degradation.

| Polymer | Approx. time for Absorption (months) |
| --- | --- |
| Polycaprolactone (PCL) | >36 |
| Poly-L-lactic acid (PLLA) | 36-60 |
| PLLA-co-GA 82:18 | 12-15 |
| Poly-DL-lactic acid (PDLLA) | 12 |
| PLLA-co-DLLA 50:50 | 12 |
| PGA-co-TMC (Maxon B) | 12 |
| Polyglycolic acid (PGA) | 6-12 |
| Poly-p-dioxanone (PDS) | 6 |
| PDLLA-co-GA (85:15) | 3-6 |
| Polyanhydrides | <3 |

It is generally preferred that the times for complete absorption of the two polymers differ by at least 8 weeks, typically by about 12 weeks to two years. The difference in the degradation rates may be selected to provide a desired effect in vivo, e.g., rapid formation of a long-lasting scaffold, or rapid formation of a scaffold that will itself degrade relatively rapidly.

Suitable polymers, which may serve as the slow or rapid-degrading polymer, include, for example: polyesters; polyphosphazenes; polyacetals; polyalkanoates; polyurethanes; poly(lactic acid) (PLA); poly(L-lactic acid) (PLLA); poly (DL-lactic acid); poly-DL-lactide-co-glycolide (PDLGA); poly(L-lactide-co-glycolide) (PLLGA); polycaprolactone (PCL); polyorthoesters; polycarbonates; ABA tri-block copolymers with A blocks of semicrystalline polyglycolic acid (PGA) and a B block of amorphous trimethylene carbonate (TMC), also known as polyglyconates, commercially available from Polysciences under the tradename MAXON B polymers; and erodible polymers, e.g., polyanhydrides. Other biodegradable polymers may also be used. Typically, polymers that lose 100% of their mass within 12 months are considered to be rapid-degrading. It is generally preferred that both polymers be thermoplastic, so that devices can be produced by conventional polymer processing techniques such as injection molding.

Generally, the slow-degrading polymer and rapid-degrading polymer are provided in a ratio of from about 80:20 to 20:80, e.g., from about 60:40 to 40:60. The composition at which a blend of immiscible polymers will be co-continuous is known as the "phase inversion point"; generally, for all other compositions of this blend of polymers, one phase will become continuous with the other dispersed within it. The volume ratio of the phase inversion point for a mixture of immiscible liquids can be predicted from the ratio of their viscosities according to the following equation, which expresses the relationship of volume ratio at phase inversion to phase viscosity:

$$\frac{\varphi_A}{\varphi_B} = \frac{\eta_A}{\eta_B}$$

η=Viscosity of polymer
φ=Volume fraction of polymer

Other factors having an effect on the morphology of the blend are the interfacial tension between the phases and the mixing conditions. Immiscible polymers will generally separate in the melt to produce two phases, a well-mixed blend forming an emulsion. The stability, phase distribution and other properties of the emulsion can be predicted from theory, if the physical properties of its components are known. Due to the high melt viscosity of polymers, changes in emulsion structure are slow, so little change in phase structure is observed during conventional extrusion or injection molding. By heating the polymer mixture above its melting point for an extended period of time, significant large-scale phase separation (50 to 1000 µm) can be achieved. The extent of phase separation can be controlled by varying the treatment time and temperature. We have found that due to the slow separation rate it is possible to produce and fix (by cooling below the melting point) co-continuous phase structures at compositions other than that of the phase inversion point.

Additives may be incorporated into either or both of the phases to modify the melt viscosity and/or biocompatibilty of the polymer, e.g., fillers such as hydroxyapatite or other calcium phosphates. Additives may be added to either or both of the polymer phases to modify the degradation rate of that phase, e.g., lauric acid. Blends of miscible polymers may also be used in one or more of the phases to achieve the desired properties.

By Infiltration of a Porous Scaffold

Alternatively, devices including two polymeric components may be formed by infiltrating a porous, pre-formed polymeric structure with either (i) a resorbable polymer, or (ii) reactive components (i.e. monomers, oligomers etc) which on initiation of a chemical reaction form a degradable polymeric matrix. In either case, one component is either non-degrading or slow-degrading in vivo (slower than the other components). Thus, as discussed above, the device is initially non-porous and thus mechanically robust, but forms an open polymeric scaffold as the faster degrading polymer degrades in vivo.

In this embodiment, the two polymers need not be immiscible, but need only have different degradation rates. Infiltration may be accomplished, for example, using techniques that will be described below under "Polymer-Ceramic Systems."

Devices Including a Polymeric Component and a Ceramic Component
(Polymer-Ceramic Systems)

Ceramic Scaffolds from Polymer/Ceramic Composites

Initially non-porous, biodegradable tissue fixation/repair devices that provide a ceramic scaffold may be formed by infiltrating a porous, pre-formed ceramic structure with (i) a resorbable polymer or (ii) reactive components (i.e. monomers, oligomers etc) which on initiation of a chemical reaction form a degradable polymeric matrix. In either case, the porous ceramic structure is either non-degrading or slow-degrading in vivo (slower than the infiltrating polymer or reactive components).

The polymer ceramic device is designed so that the polymeric phase will degrade preferentially, to produce a ceramic scaffold that fills with bone or other tissue. The ceramic phase may also subsequently degrade, resulting in the complete replacement of the device by bone or other tissue. The device will thus eventually either be replaced completely by bone, or be replaced partially by bone, to yield a bone-filled ceramic scaffold.

The mode of degradation of the polymer will also influence the structure that is formed in situ. Mode of degradation will generally fall into one of the following categories: (i) the polymer bulk degrades to form an open ceramic scaffold, which then fills with bone; in this model bone does not grow into the ceramic structure until most of the polymer has degraded; or (ii) the polymer surface erodes to generate pores which bone grows into; in this model bone will supplement the strength of the device by replacing polymer as the polymer degrades.

Suitable polymers capable of fully infiltrating the macro- and micro-pores of the pre-formed porous ceramic structure include but are not limited to: Poly($\alpha$-hydroxy acids), e.g., (polylactides, polyglycolides, polycaprolacatones, polydioxanones, polyhydroxyalkonates, polycarbonates, polyacetals, polyorthoesters, polyamino acids, polyphosphoesters, polyesteramides, polyfumerates, polyanhydrides, polycyanoacrylates, polyoxomers, polysaccharides, collagen, and polyurethanes. These polymers may take the form of homopolymers or copolymers (i.e. random, block) or blends thereof. The polymer can have any desired structure, e.g., linear, star, branched and the like. Examples of suitable polymer and ceramic combinations, chosen so that the polymer will degrade faster than the ceramic, include Polyglyconate B with tricalcium phosphate (TCP), and PLA with hydroxyapatite (HA).

Suitable reactive monomers/oligomers include those typically used to form the above polymers, for example cyclic esters, e.g., lactides, glycolides and caprolactone, cyclic carbonates, divinyl ethers-diols, disocyanate-diamine, and the like. Suitable monomers typically melt to produce a water-like consistency, i.e., the monomers have very low melt viscosities. Thus, generally little or no solvent is required to moderate the melt viscosity of the monomer, and the monomer is able to penetrate completely into the pores of the ceramic scaffold.

The ceramic preform should have sufficient structural integrity to withstand infiltration by the polymer or reactive monomers/oligomers and to provide desired structural properties in situ as the polymer degrades and tissue ingrowth occurs. In some implementations, the preform has a compression strength of at least 1 MPa, e.g., at least 3 MPa.

The polymer or reactive monomers/oligomers can be infiltrated into the ceramic preform using any desired technique, for example by injection molding or reactive processing. Molding pressures may be adjusted to avoid damage to the preform and to ensure adequate infiltration. Typical molding pressures are from about 500 to 2000 psi.

Polymeric Scaffolds from Polymer/Ceramic Composites

Alternatively, the polymer/ceramic composites discussed above may be designed so that the ceramic degrades preferentially in vivo, rather than the polymer, resulting in a polymeric scaffold. The ceramic surface erodes (by dissolution, or by being eroded by cells) to generate pores which bone grows into. This model allows bone to supplement the strength of the device by replacing ceramic as it degrades. To achieve this, a polymer/ceramic combination is selected in which the ceramic will have a more rapid degradation rate than the polymer. The polymer phase may also subsequently degrade, resulting in complete replacement of the device by bone or other tissue.

Suitable polymers capable of fully infiltrating the macro- and micro-pores of the pre-formed porous structure include the polymers discussed above in the "Ceramic Scaffolds from Polymer/Ceramic Composites" section. Examples of suitable polymer and ceramic combinations, chosen so that the ceramic will degrade faster than the polymer, include PLA with TCP and PCL with TCP.

Suitable reactive monomers/oligomers include those discussed above in the "Ceramic Scaffolds from Polymer/Ceramic Composites" section.

Devices Including Two Ceramic Components (Ceramic-Ceramic Systems)

Initially non-porous, biodegradable tissue fixation/repair devices that provide a ceramic scaffold may also be formed by infiltrating a porous, pre-formed ceramic structure with a ceramic material that forms a degradable ceramic matrix. One component is either non-degrading or slow-degrading in vivo (slower than the other component).

Suitable ceramics include calcium phosphates such as hydroxy apatite, tricalcium phosphate, octacalcium phosphate, dicalcium phosphate dihydrate; calcium sulfate; beta dicalcium pyrophosphate; and calcium carbonate. Other suitable ceramics include biocompatible glasses such as Bioglass. Examples of suitable combinations include hydroxyapatite with tricalcium phosphate, hydroxyapatite with calcium sulfate, tricalcium phosphate with calcium sulfate (in these examples the first material is the slower degrading component). The composites can be made by infiltrating a porous pre-formed structure formed of one ceramic with the other ceramic component in the form of a slurry. This second component may be a ceramic in a settable cement form e.g. calcium sulfate (plaster of Paris).

Generally, preferred scaffolds have a pore size of about 20-2000 microns, preferably about 50-1000 microns, and a porosity of about 10-90%, preferably about 50-85%. The degradable ceramic used to infiltrate the scaffold preferably has a particle size that is sufficiently large to allow cell infiltration, typically less than 100 μm. The particle size of the ceramic used to form the scaffold is typically from about 1 nm to 1 mm.

The following examples are intended to be illustrative and not limiting in effect.

Example 1

Polymeric Scaffold Formed by Phase Separation 50 grams each of PGA and PLLA were dried under vacuum at 110° C. overnight. The polymer granules were then dry mixed before use. A twin-screw extruder was used to melt mix the polymer at 245° C. The blend was extruded in the form of a rod 6 mm in diameter.

2 cm lengths of the polymer rod were subjected to melt induced phase expansion (MIPE) treatment in a heated press at 230° C. or 235° C. in a cylindrical mold (6 mm diameter, 20 mm long). The mold was placed in the press and the press closed with a force of 50 kN. Once the sample had received the required treatment time, the mold was removed from the press and immersed in cold water to rapidly cool the sample. The treated rods were approximately 5.7 mm in diameter due to shrinkage on cooling. The rods were cut to produce a series of 1 mm thick slices using a diamond bladed saw.

Figure 2:
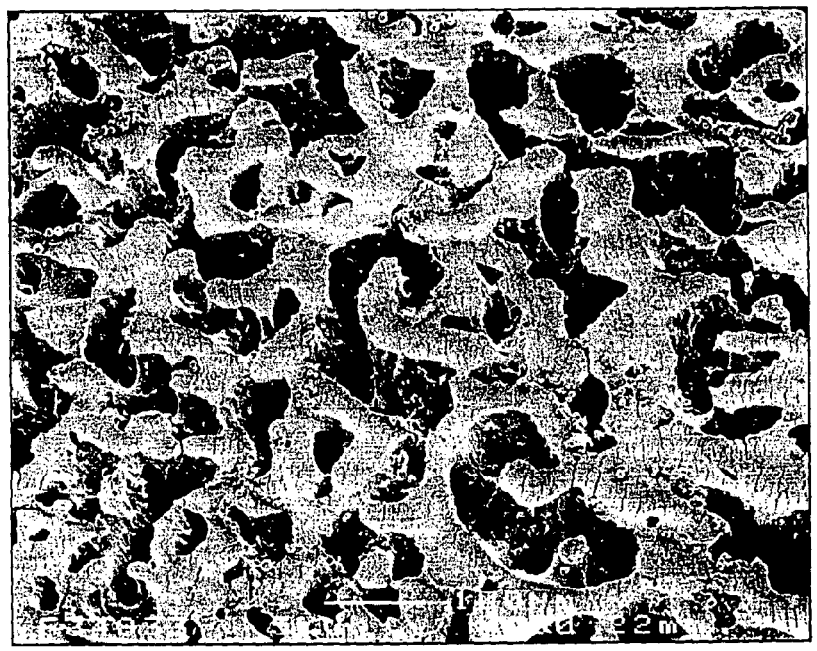

Slices of each sample were subject to accelerated degradation in PBS at 70° C. After 29 days, the samples were removed from the PBS, rinsed with deionised water and dried in a vacuum oven at 110° C. The samples were then examined by SEM to reveal the porous structure generated by the PGA degrading out of the PLLA. The dimensions of the pores produced were between 1 and 200 μm depending on the MIPE treatment conditions; examples of the porosity observed are shown in FIGS. 1 and 2. The pore size was observed to increase in size with MIPE treatment temperature and time.

Example 2

Polymeric Scaffold Formed by Infiltration 5 grams of PLLA were placed in a small (15 ml) membrane filter housing with no membrane fitted. The granules were washed with 2×10 ml of $CH_2Cl_2$ and the residual solvent removed by applying a vacuum to the filter. The wet granules were packed into a 30 ml pot, to produce a pellet molded to the shape of the pot, then placed in an oven at 60° C. After 1 hour, the samples were transferred to a vacuum oven and heated to 100° C. at 5 mbar for 2 hours. The samples were then left under vacuum over night. The cylindrical blocks (24 mm diameter by 14 mm) produced had a porosity of 49±5% ($^v/_v$) with pore dimensions of 0.5 to 3.5 mm.

Poly(sebacic anhydride) (PSA) was melted in an oven at 120° C. Two porous PLLA blocks were placed in 30 ml PTFE pots then heated in an oven at 100° C., the liquid PSA then was poured into the pots containing the blocks. The filled pots were then transferred to a vacuum oven at 100° C. and a vacuum of 0.87 mbar applied to remove any air bubbles. The samples were then removed from the oven and allowed to cool. Once the PSA had solidified, the composite samples were removed from the pots and cut using a precision diamond saw to produce slices 4 mm thick.

Slices of composite were placed in PBS at 37° C., for up to 75 days. The PSA was observed to erode out of the PLLA to leave pores of 0.5 to 3.5 mm.

Example 3

Ceramic Scaffold

Figure 3:
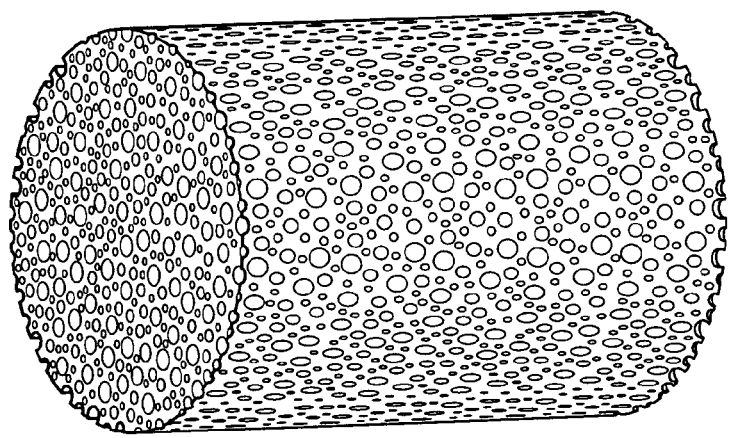
FIG. 3 is a perspective view of a ceramic plug used in the procedure described in Example 3.

A number of cylindrical plugs of hydroxy apatite were provided, each plug having interconnecting pores ranging from 100 to 1000 μm in diameter. An example of such a plug is shown diagrammatically in FIG. 3.

Each plug was placed in a mold that included elongated ribs that supported the plug by contacting the plug axially. The ribs were positioned at four locations that were evenly spaced around the circumference of the plug. Each ribs was approximately 0.050 inch high, creating a gap of 0.050 inch between the mold surface and the outer surface of the plug. The ribs were approximately 0.050 inch wide, and extended substantially the entire length of the plug.

Figure 4:
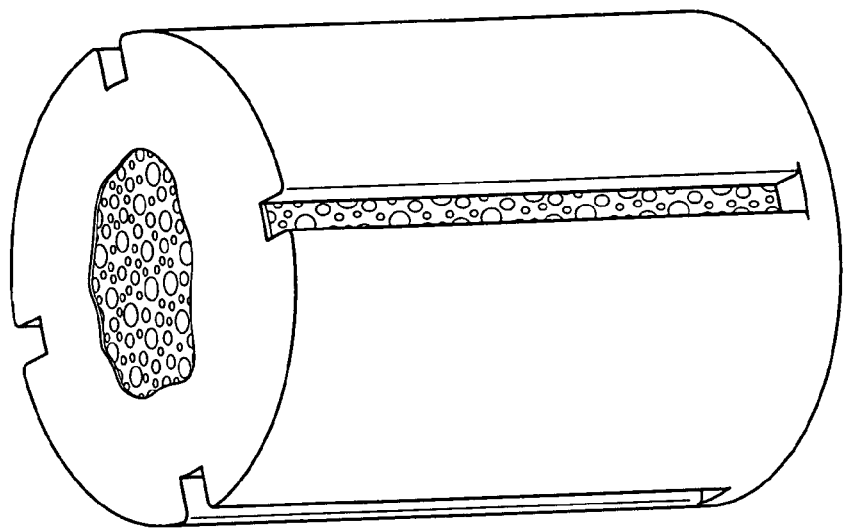
FIGS. 4 and 4A are perspective and cross-sectional views, respectively, of a device resulting from the procedure described in Example 3.
Figure 4A:
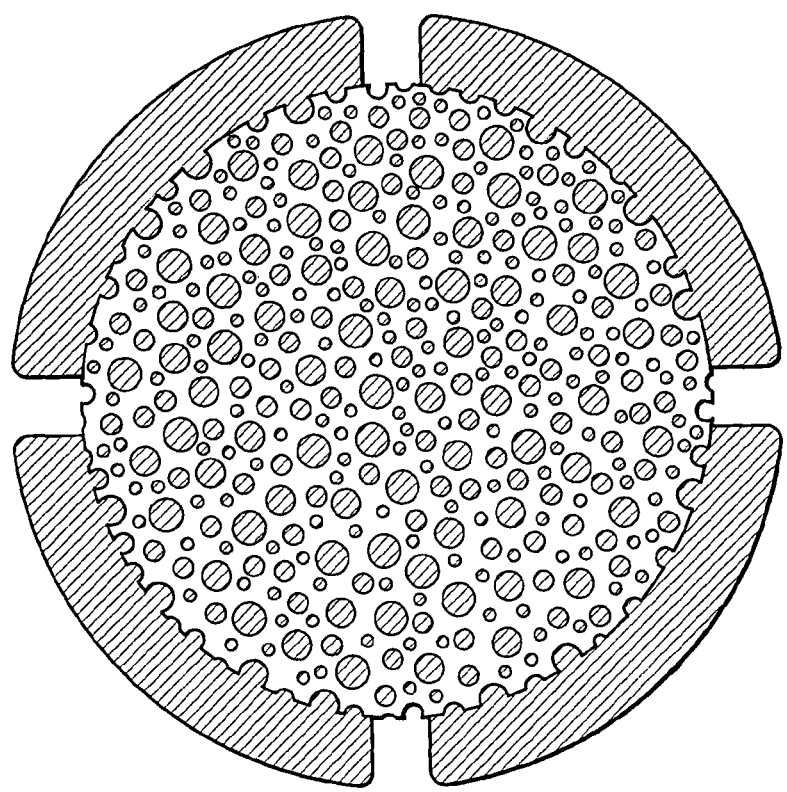

Poly-glyconate B polymer was then injection molded into and around each plug. Standard melt processing temperatures were used, i.e., 410-435° F. Using different plugs, injection molding was conducted at pressures of 600, 800, 900 and 1000 psi, to examine the effect of pressure on filling of the pores. At each molding pressure, the interconnecting pores were filled throughout the entire plug, and a 0.050 inch layer of polymer was provided around the implant in the areas where there was a gap between the mold and plug due to the presence of the supporting ribs. The outer surface of the plug was exposed in the areas where the ribs contacted the plug. A plug formed using this procedure is shown diagrammatically in FIGS. 4 and 4A.

Example 4

PDLLA-TCP In Situ Composites

Preparation of Glassware

Custom made flat-bottomed glass tubes (14 cm long×24 mm ID) with a 24/29 quick fit tops were used for the polymerization. The tubes were washed with deionized water, dried in an oven at 105° C. and allowed to cool in a desiccator. The tubes were filled with Dichlorodimethylsilane and sealed, then allowed to stand overnight with occasional shaking. The tubes were then emptied and rinsed three times with dry ether. After allowing the bulk of the residual ether to evaporate (5 mins) in the fume cupboard, the tubes were transferred to a vacuum oven at 150° C. approx. 5 mbar.

All other glassware, stoppers, seals and equipment used with reagents was washed with deionized water, dried at 105° C. and stored in a desiccator prior to use.

Preparation of Catalyst in Initiator Solution

All preparation was done under a dry nitrogen atmosphere in an Atmosbag. 1.00 g of $SnCl_2.2H_2O$ and 2.91 g (2.60 ml) of Di(ethyleneglycol) were weighed into a 10 ml Wheaton vial. The vial was sealed prior to removal from the Atmosbag, and shaken to produce a clear solution.

Preparation of Ceramic

Tricalcium phosphate blocks were cut to produce cylinders that would fit in the reaction tubes using an Isomet low speed saw fitted with a diamond-wafering blade using deionised water as a cutting fluid. The blocks were then rinsed with deionized water to remove any loose fragments of ceramic and dried in the vacuum oven at 105° C. approx. 5 mbar for 2 hours.

In Situ Formation of Polymer/Ceramic Composite

The dried ceramic blocks were placed in the reaction tubes, the tubes were sealed with suba seals vented with syringe needles. The vented tubes were then placed in the vacuum oven and a vacuum of approx 5 mbar was then applied. The oven was then re-pressurized with dry nitrogen and the tubes transferred to a conventional oven at 150° C. shortly before they were to be used. The reaction tubes were processed in sets of up to 10 tubes.

10 µl of catalyst/initiator solution was added to each tube, with the monomer, after which the tubes were placed in an oven at 150° C. Once the monomer had melted, the tubes were filled and sealed under a dry nitrogen atmosphere in an Atmos bag. Before the tubes had cooled, with the monomer still liquid, the tubes were vented with syringe needles and placed in a preheated vacuum oven at 150° C. A vacuum of approx. 5 mbar was then applied for 15 minutes to ensure that all air bubbles were removed from the ceramic. The oven was then re-pressurized with dry nitrogen, the tubes removed and the syringe needles taken out immediately. The tubes were then placed in a conventional oven at 147° C. (oven set at 155° C.). The samples were left in the oven for approx. 5.5 days; the oven was then switched off and the samples allowed to cool. The samples were then bagged up under dry nitrogen and placed in the freezer.

Machining of Samples

Pipe grips were used to remove cracked glass tube from sample. A Smart & Brown center lathe with a 3-jaw chuck was used. A high speed steel, right hand knife tool was used to turn the material down to the required diameter, initially a spindle speed of approx. 500 rpm but this was subsequently reduced to 250 rpm. The screw thread was cut using c a 50 rpm spindle speed and a H.S.S. tool 1.5 mm wide and with a small radius on the end. A large pitch was selected 3.6 mm and the depth was decided on looks only after a series of 0.2 mm cuts were taken. No cutting fluid was used.

A number of embodiments of the invention have been described. Nevertheless, it will be understood that various modifications may be made without departing from the spirit and scope of the invention. Accordingly, other embodiments are within the scope of the following claims.

For example, if desired, the device may include more than two phases. For example, the device may include two polymeric phases and a ceramic phase.

Moreover, if desired, the polymers discussed above may contain therapeutic additives that are released during the degradation or erosion of the polymer or by diffusion from the polymer phase. If the additive is used in a polymer that forms the scaffold, the additive may migrate to the polymer surface of the scaffold structure.

The therapeutic additive may be provided in a physiologically acceptable carrier, and may be provided in sustained release or timed release formulations. The additives may also incorporate agents to facilitate their delivery, such as antibodies, antibody fragments, growth factors, hormones, or other targeting moieties, to which the additives are coupled. Suitable carriers, additive dosages, and methods of incorporating the therapeutic additive are described, e.g., in U.S. Pat. No. 6,337,198, the disclosure of which is incorporated herein by reference.

Suitable additives include biologically or pharmaceutically active compounds. Examples of biologically active compounds include cell attachment mediators, such as the peptide containing variations of the "RGD" integrin binding sequence known to affect cellular attachment, biologically active ligands, and substances that enhance or exclude particular varieties of cellular or tissue ingrowth. Such substances include, for example, osteoinductive substances, such as bone morphogenic proteins (BMP), epidermal growth factor (EGF), fibroblast growth factor (FGF), platelet-derived growth factor (PDGF), insulin-like growth factor (IGF-I and II), TGF-beta and the like.

Examples of pharmaceutically active compounds include, for example, acyclovir, cephradine, malfalen, procaine, ephedrine, adriomycin, daunomycin, plumbagin, atropine, guanine, digoxin, quinidine, biologically active peptides, chlorin e.sub.6, cephalothin, proline and proline analogues such as cis-hydroxy-L-proline, penicillin V, aspirin, ibuprofen, steroids, nicotinic acid, chemodeoxycholic acid, chlorambucil, and the like.

The additives may be used alone or in combination with other therapeutic or diagnostic agents.

In some implementations, the tissue fixation device may be formed by providing a pre-formed porous polymeric structure, and infiltrating it with a slurry of a ceramic material that is selected to dissolve or to be eroded by cells at a rate that is slower than the degradation rate of the polymer, so that a ceramic scaffold is formed as the polymer degrades.

While bone fixation devices are discussed above, the composites discussed herein may be used in other applications, for example as materials for maxillo-facial reconstruction, and as bone graft substitutes, e.g. for spinal fusion or for void filling following bone loss due to tumor resection, trauma, joint replacement or other causes. The composites may also be used for repair and/or replacement for tissues such as cartilage, ligaments and tendons, and other soft tissue repair such as rotator cuff repair.

What is claimed is:

1. A biodegradable tissue fixation device, comprising:
   a first component comprising a polymer, having an outer surface and having interconnecting pores;
   a second component disposed in the pores of the first component, such that the first component is non-porous;
   wherein the second component further forms a non-porous layer that covers the outer surface of the first component except in defined areas; and
   wherein the first component has a higher rate of in vivo degradation than the second component.

2. The device of claim 1, wherein the first component has a pore size of about 20-2000 microns.

3. The device of claim 1, wherein the first component has a porosity of about 10-90%.

4. The device of claim 1, wherein the second component comprises a ceramic.

5. The device of claim 1, wherein the second component comprises a polymer.

6. The device of claim 1, wherein the first component comprises a polymer selected from the group consisting of poly(a-hydroxy acids), polyhydroxyalkonates, polycarbonates, polyacetals, polyorthoesters, polyamino acids, polyphosphoesters, polyesteramides, polyfumerates, polyanhydrides, polycyanoacrylates, polyoxomers, polysaccharides, collagen, polyurethanes, and mixtures thereof.

7. The device of claim 1, wherein there is at least an 8 week difference between the rate of in vivo degradation of the first and second components.

8. The device of claim 7, wherein the rate of in vivo degradation of the first and second components differs by about 12 months to 2 years.

9. The device of claim 1, wherein at least one of the first and second components includes a therapeutic additive.

10. The device of claim 5, wherein the second component comprises a polymer selected from the group consisting of poly(a-hydroxy acids), polyhydroxyalkonates, polycarbonates, polyacetals, polyorthoesters, polyamino acids, polyphosphoesters, polyesteramides, polyfumerates, polyanhydrides, polycyanoacrylates, polyoxomers, polysaccharides, collagen, polyurethanes, and mixtures thereof.

11. The device of claim 10, wherein the polymer comprises a poly(hydroxyl acid) selected from the group consisting of polylactides, polyglycolides, polycaprolacatones, polydioxanones, and a mixture thereof.

12. The device of claim 5, wherein the polymer comprises Polyglyconate B and the ceramic comprises tricalcium phosphate (TCP).

13. The device of claim 5, wherein the polymer comprises poly(lactic acid) and the ceramic comprises hydroxyapatite (HA).

14. The device of claim 1, wherein the polymer is formed by reacting in situ a reactive monomer or oligomer.

15. The device of claim 14, wherein the reactive monomer is selected from the group consisting of cyclic esters, cyclic carbonates, divinyl ethers-diols, disocyanatediamine and mixtures thereof.

16. The device of claim 1, wherein the non-porous layer is 0.050 inches in thickness.

17. The device of claim 6, wherein the polymer comprises a poly(hydroxyl acid) selected from the group consisting of polylactides, polyglycolides, polycaprolacatones, polydioxanones, and mixtures thereof.

18. The device of claim 1, wherein the defined areas are the areas where ribs of a production mold contacted the outer surface of the first component.

* * * * *